United States Patent [19]
Yu

[11] Patent Number: 5,779,907
[45] Date of Patent: Jul. 14, 1998

[54] MAGNETIC MICROPLATE SEPARATOR

[75] Inventor: Hao Yu, Baltimore, Md.

[73] Assignee: Systems Research Laboratories, Inc., Dayton, Ohio

[21] Appl. No.: 761,593

[22] Filed: Dec. 6, 1996

[51] Int. Cl.$^6$ ................................................. B01D 35/06
[52] U.S. Cl. .......................... 210/695; 210/222; 436/526
[58] Field of Search .................................. 210/222, 232, 210/695; 435/173.1; 436/523, 526

[56] References Cited

U.S. PATENT DOCUMENTS 4,988,618  1/1991  Li et al. .............................. 435/173.1
5,567,326  10/1996  Ekenberg et al. ...................... 210/695

OTHER PUBLICATIONS

Biomagnetic Techniques in Molecular Biology, pp. 138–139 1995.
Biomagnetic Applications in Cellular Immunology pp. 1–3 (undated).
Magnetic Equipment, "R1", Dynal (1 page) (undated).
Microlite and MicroFLUOR Multiple Sample Disposable Plasticware (1 page) Dynatech Laboratories.
Permanent Magnets for Magnetic Separations, BioMag (one page) (undated).

*Primary Examiner*—David A. Reifsnyder
*Attorney, Agent, or Firm*—E. Paul Forgrave

[57] ABSTRACT

An apparatus for immunoassay using a 96-well microplate includes a mechanism for supporting the microplate in a relatively fixed position, a magnetic microplate assembly containing multiple cylindrical magnets positioned in 4×6 arrays for insertion from the bottom of the microplate in the spaces between the wells of the microplate, and a device for moving the magnet microplate assembly relative to the microplate thereby to permit selective separation of magnetic components within the microplate wells. The magnets, preferably cylindrical in configuration, are placed between groups of four wells in the microplate. The magnetic microplate assembly is reusable. The magnets do not come into contact with any of the fluids within the wells of the microplate.

12 Claims, 5 Drawing Sheets

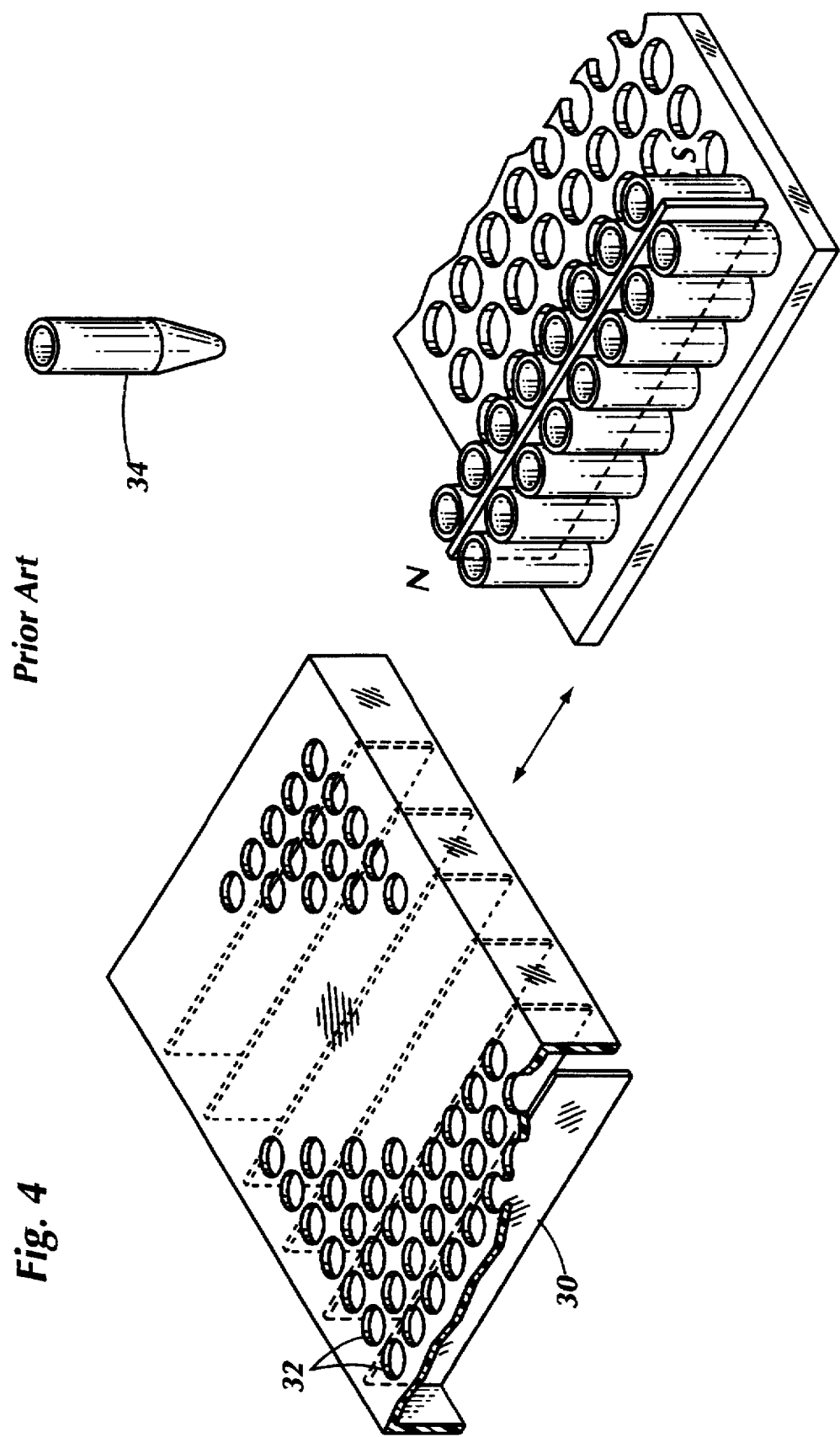

Insert

Remove

Wash

MAGNETIC MICROPLATE SEPARATOR

BACKGROUND OF THE INVENTION

This invention relates to an improved device for applying a strong magnetic field to liquids in a multiple-sample microplate.

Use of biological activated magnetic particles as a carrier for biological agent separation and purification has received great attention by researchers since late 1970's. The Dynal Company of Lake Success, N.Y. has developed several biological (e.g. antibody coated) and chemical activated (e.g. Tosyl group or Amino group) magnetic particles to help researchers develop novel approaches for antigen, cells separation and purification purposes in the field of molecular biology, microbiology and cellular immunology. Since magnetic separation does not necessarily require a sophisticated instrument, only one permanent magnet and the magnetic particles in solution are required for particle separation.

Currently, several magnetic separators in the commercial market are available. As an example, the Dynal and Advanced BioMag's magnetic equipments covered the most types of magnetic separators including hand-held and mixing separators.

However, as the rapid development of cutting edge biotechnologies for those who work with infectious disease agent, large workload hospitals, clinical labs, and even in research labs, for large workload DNA sequencing work, avoiding the multiple and unnecessary handling of harmful biological agents while obtaining consistent experimental results have become critical and important in their daily work. Therefore, a semi-automated, programmable, multiple sampled magnetic separator is needed to satisfy these requirements.

SUMMARY OF THE INVENTION

The present invention proposes to fulfill a need in the industry by making magnetic separation available for use with a disposable multiple-sample microplate. One such microplate plate is manufactured by Dynatech Laboratories of Chantilly, Va. A microplate is a commercially available container for fluids that includes multiple wells, each formed with the wells extending downwardly from the plate's upper surface. Due to the construction of the microplate, and particularly the close spacing between the wells, prior art magnetic separation equipment and techniques cannot be used.

The present invention, on the other hand, comprises a magnetic microplate separator that includes a plurality of individual magnets which are placed in the spaces between four associated wells. This arrangement provides certain advantages; namely, each well is adjacent a strong magnet which has both a north and a south pole adjacent the side of the well; the magnetic elements in the fluid are drawn to the sides of the wells, not the bottom; a stronger magnet can be used; an alternate N-S pole arrangement may be used; and the magnets may be mounted on a non-magnetic plate to provide proper spacing as the microplate is lowered into place. The magnetic microplate separator is reusable. Also, magnet plates for microplates having a different number of wells may be provided.

It is therefore an object of this invention to provide a magnetic microplate separator for use with a microplate provided with multiple wells for containing liquid under analysis, comprising a support plate, and a plurality of magnets supported on the support plate and extending upwardly into the spaces formed between the wells of the microplate from underneath the microplate. In one embodiment, a single cylindrical magnet is inserted between four wells of the microplate.

It is another object of this invention to provide an apparatus for immunoassay using a microplate including means for supporting the microplate in a relatively fixed position, a magnet microplate separator containing multiple magnets positioned for insertion in the spaces between wells in the microplate, means for moving the magnet microplate relative to said microplate thereby to permit selective separation of magnetic components within the microplate wells.

It is still a further object of this invention to provide a method of separating suspended magnetic particles in a microplate comprising the steps of supporting a plurality of individual magnets on a plate with each magnet being capable of being inserted into the space between four wells of the microplate and inserting the magnet containing plate into the underneath side of the microplate.

Other objects and advantages of the invention will be apparent from the following description, the accompanying drawings and the appended claims.

BRIEF DESCRIPTION OF THE DRAWINGS

FIG. 4 is a perspective view of a prior art device showing individual cups in a well plate, and associated strip magnets placed between the cups;

DESCRIPTION OF THE PREFERRED EMBODIMENT

Figure 1:
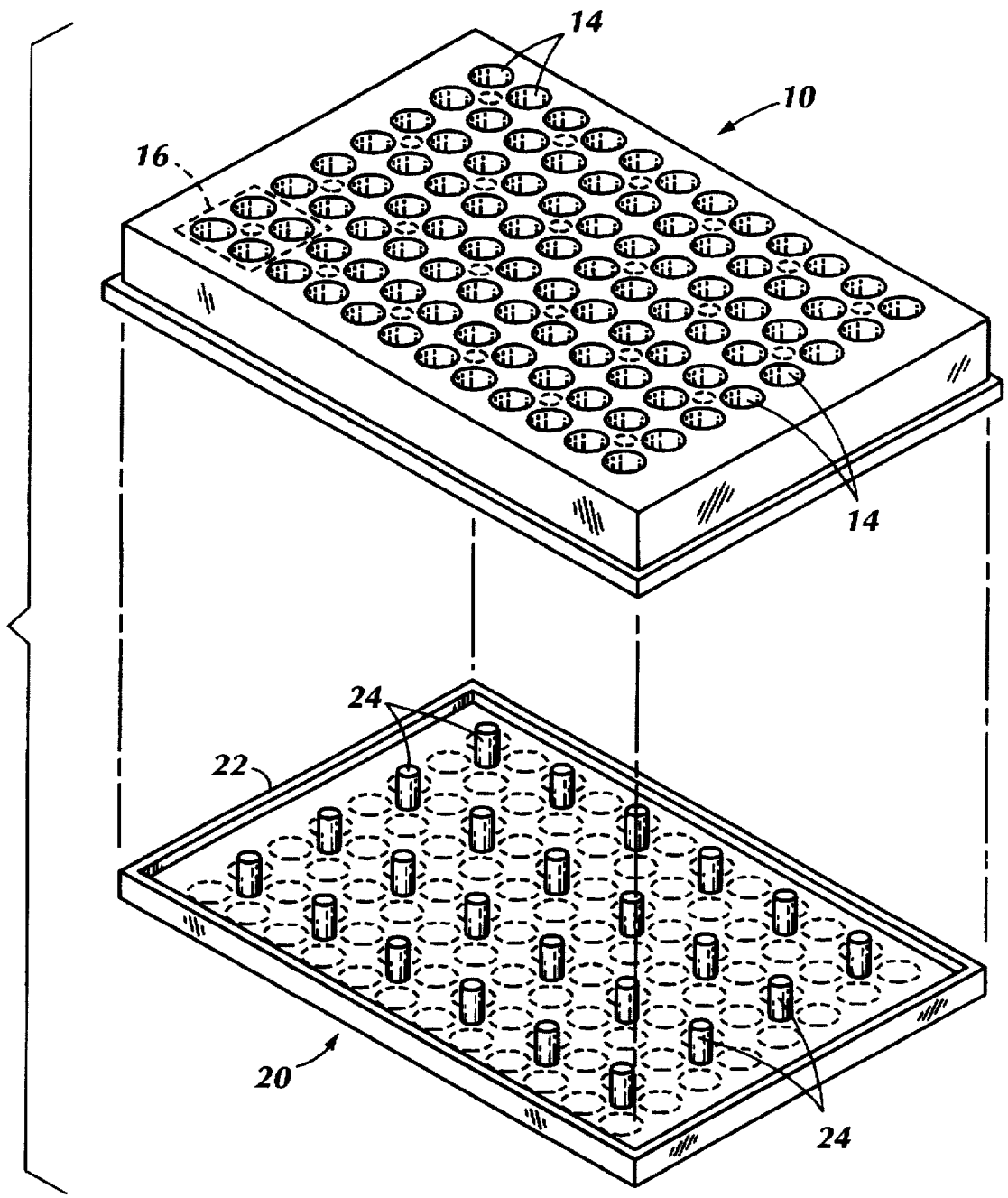
FIG. 1 is a perspective view of a typical 96-well microplate and a magnet microplate separator spaced therebelow.
Figure 2:
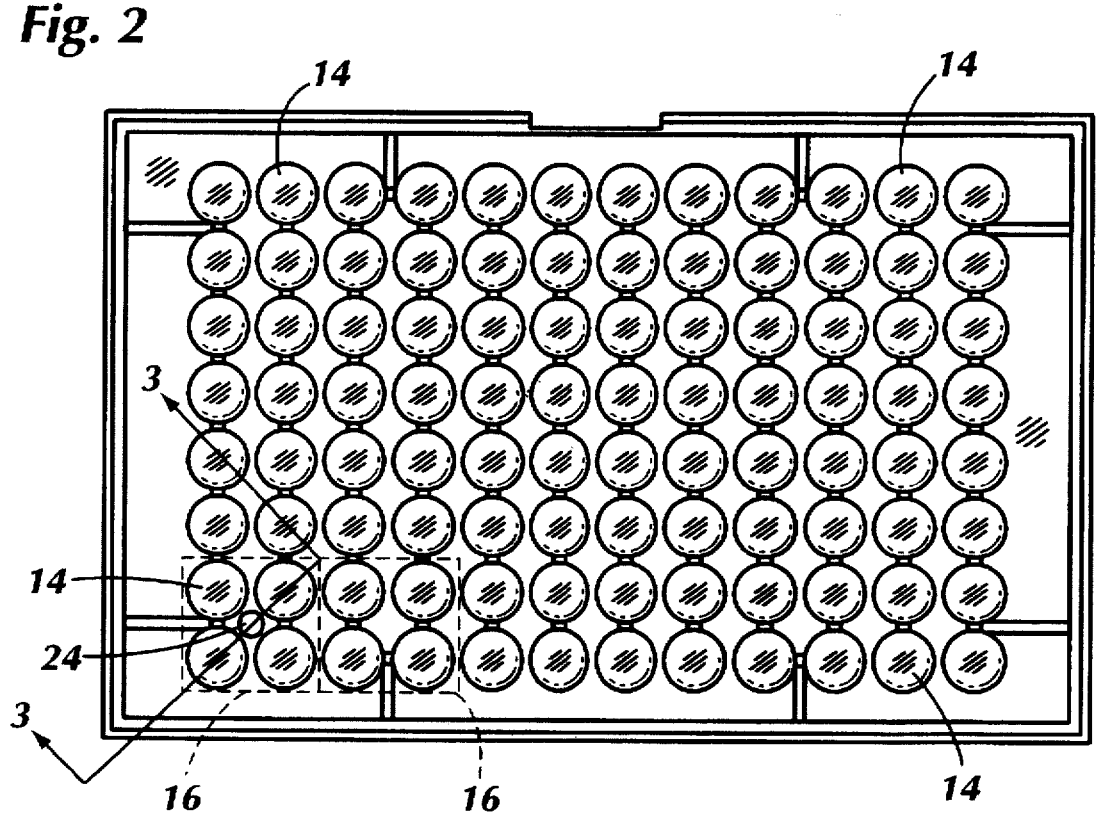
FIG. 2 is a bottom plan view of a microplate that is used in connection with the present invention.

Referring now to the drawings, and particularly to FIGS. 1 and 2, a typical disposable microplate 10 is formed from a single sheet which has an upper surface 12 and integrally formed multiple wells 14 for holding liquid samples. As shown, the wells 14 in microplate 10 are arranged in an 8 by 12 array.

A reusable magnet microplate assembly 20 is shown in FIG. 1 positioned below the microplate 10. The plate assembly 20 includes a support plate 22 on which is mounted a plurality of individual magnets 24. In the preferred embodiment of this invention, there is one magnet 24 for each group 16 of four wells. Thus, for a ninety-six well microplate, the magnet microplate assembly will include twenty-four magnets 24. While a ninety-six well microplate is illustrated, this invention is equally applicable to standard 6, 12, 24, 48 tissue culture plates.

The magnets 24 are preferably cylindrical and can be fabricated from many different materials, including Alnico or rare earth materials in order to provide strong magnetic fields adjacent the wells 14. The poles of the magnets are at the ends, and the polarity of the magnets may alternate. The ninety-six well magnetic microplate separator 20 shown in FIG. 1 was fabricated preferably using a 4×6 array of individual rod-shaped magnets. Alternatively, a 5×7 array, or some other configuration could also be employed.

Figure 3:
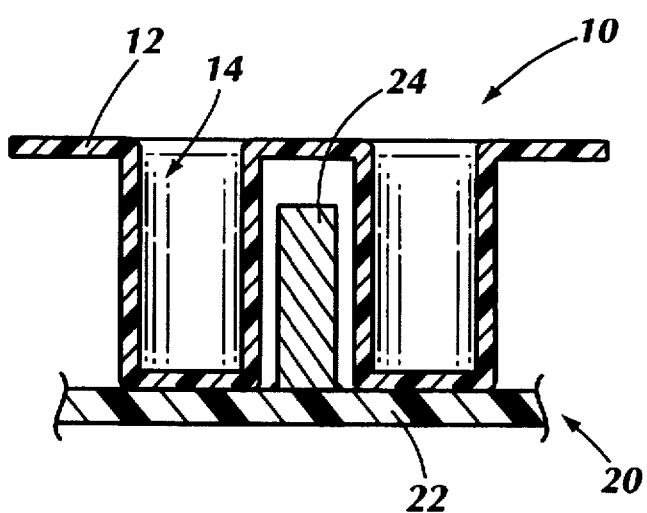
FIG. 3 a cross-sectional view of a microplate showing a magnet inserted between wells.

Referring to FIG. 2, which shows the underneath side or bottom of a microplate 10, it is noted that the individual wells 14 are closely spaced. In some microplate designs, the walls of the wells 14 actually touch adjacent wells; thus, there is no space between the wells in which to insert a strip magnet, as in prior art systems. There is, however, space between groups of four wells, in which to place a magnet 24. FIG. 3 is a cross-sectional view showing a magnet 24 positioned between wells 14 when the plate assembly 20 is nested with the microplate 10.

The plate 22 is preferably formed of a non-magnetic material, such as plastic, approximately 1 mm thick. The magnets 24 are typically 6.25 mm long and approximately 3.15 mm in diameter.

A prior art system is illustrated in FIG. 4. This device includes a frame 30 provided with a array of holes 32 into which individual containers 34 are inserted. Strip magnets 40 may be inserted between the installed containers to provide magnetic separation.

Figure 5A:
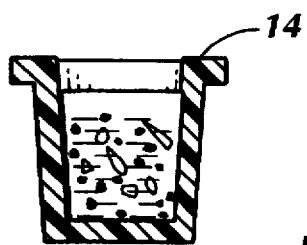
FIGS. 5A, 5B and 5C are side elevational views of a single well during different phases of a process to illustrate how magnetic particles are disbursed in a liquid with and without a magnet.
Figure 5B:
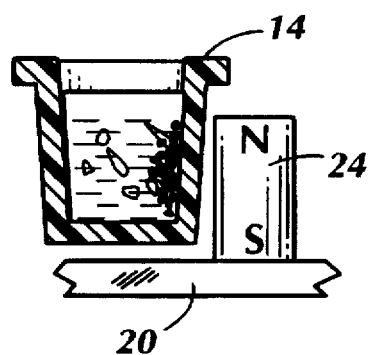
Figure 5C:
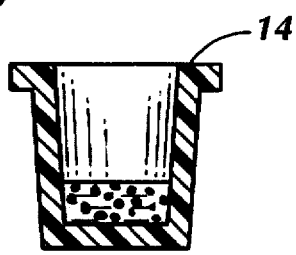
Figure 6:
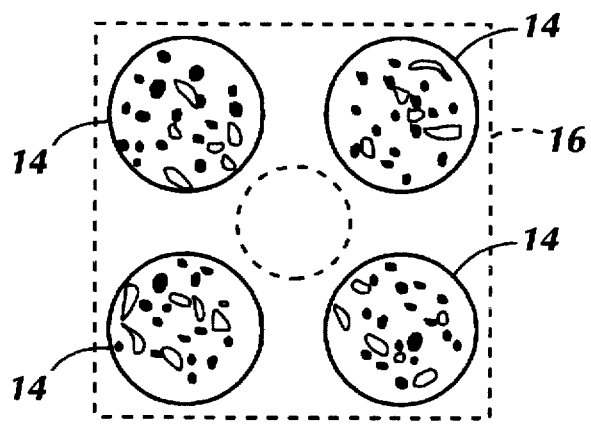
FIG. 6 is a top plan view of a set of four wells showing the distribution of magnetic particles without a magnet present.
Figure 7:
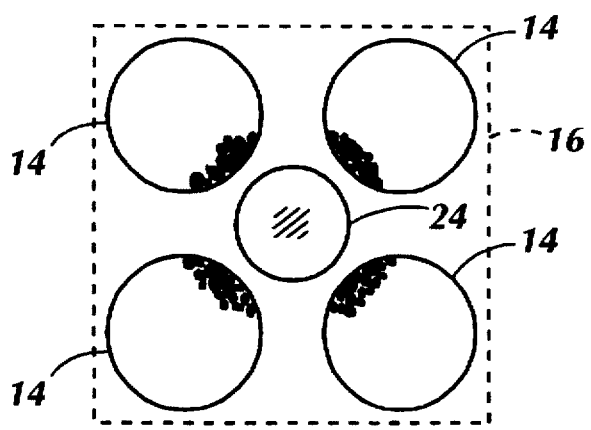
FIG. 7 is a top plan view of the four wells of FIG. 8 with a magnet present.

A typical application of this invention involves the use of an antibody coated magnetic particles 45 which are added to a liquid. A specific application will be described later, but generally speaking, the antibody coated magnetic particles are added to a solution (FIGS. 5A and 6) where a reaction takes place between the antibody and free antigen in the solution. The magnetic particles 45 are then drawn to the side of the container by a magnet (FIGS. 5B and 7); this permits the remaining solution to be removed or washed. The magnet is removed (FIG. 5C) and the magnetic particles are returned to the solution where they can be subjected to further processing.

While the general process is well known it has not been possible to use a disposable microplate for this purpose because of the impossibility of providing a strong magnetic field at the side of the wells containing the coated particles.

Figure 8:
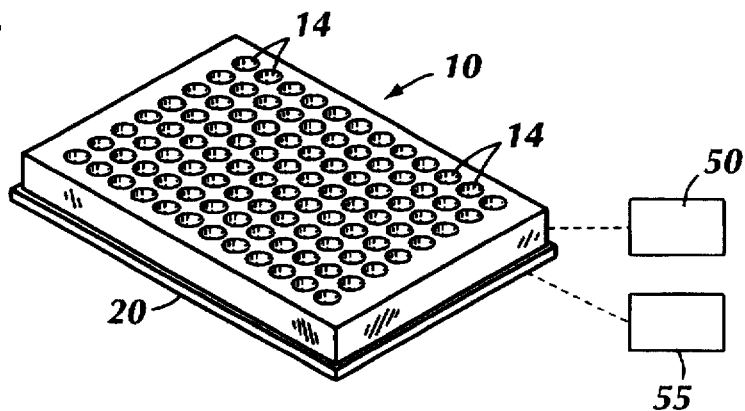
FIG. 8 is a perspective view of a microplate and magnet plate joined.
Figure 9:
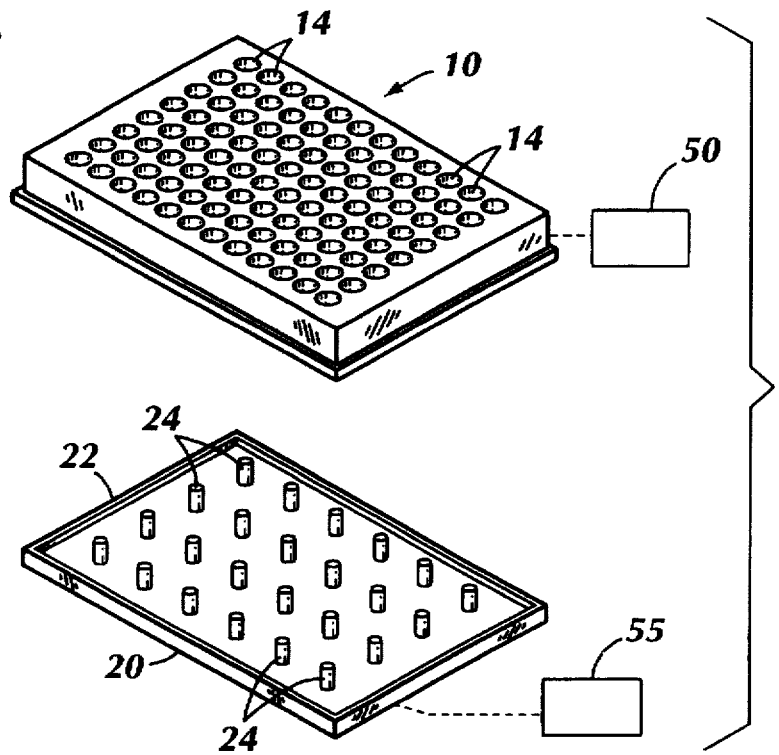
FIG. 9 is a perspective view showing the microplate and the magnet plate separated.
Figure 10:
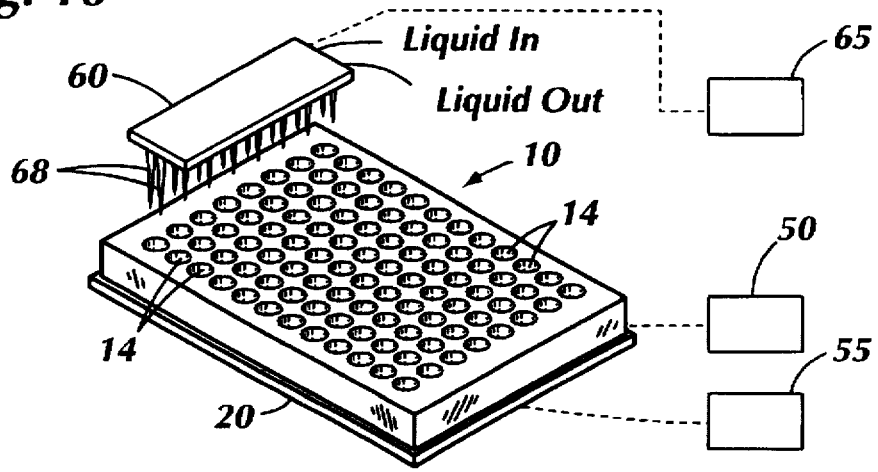
FIG. 10 is a perspective view of the microplate and magnet plate joined, and a washing unit positioned above.

Reference is now made to FIGS. 8 to 10 which shows an typical apparatus using a microplate in an immunomagnetic separation process. A microplate 10 is secured to a shaker table 50, and the magnet microplate assembly 20 is attached to an elevator mechanism 55, which comprises means for moving the magnet microplate assembly relative to the microplate thereby to permit selective separation of magnetic components within the wells of the microplate. A conventional liquid insertion and removal assembly 60 is attached to an elevator 65. From time to time during the process, the assembly 60 is lowered to place pairs of hollow needles 68 into individual wells.

A principal advantage of the present invention is that a single, disposable microplate is used throughout an immunomagnetic separation process without unnecessary handling by an operator. Sample dilution, incubation, soaking, orbital shaking, magnetic separation, bead wash, rinse and reagent dispensing in the magnetic separator may be accomplished automatically under computer program control.

After the magnetic separator is applied to the 96 well plate, the immuno-magnetic particles in each well are separated on the side wall of each well. This separation is an advantage because the agent will be separated from unwanted materials which have settled on the bottom of each well based upon the gravity. The materials on the bottom of the well are then removed by extensive washing. The remaining magnetic particles are suspended in a small volume in buffer.

The following is an example of one specific application using the present invention. The materials used are:
A Dynatech 96-well removawell holders (011-010-6604) and surface unenhanced clear optical polymer Immuolon-1 (011-010-6205) for magnetic plate (MP) fluorimmunoassay (FIA). Dynal polysterne M-280 streptavidin-coated (SA)-magnetic particles (containing 15% magnetic), antigen, biotinylated antibody, fluorochrome labelled antibodies (Ab-FITC, CY3, CY5) or alkaline phosphatase conjugated antibody, fluorgenic substrate and Super-blocking solution (Pierces) were used in the MPFIA.

The procedures used are:
1. Preparation
   1.1 To coat 96-well plates use of 0.35 ml Super-Block in TBS solution in each well for 2 hours at room temperature or overnight at 4° C.;
   1.2 To make magnetic particle working concentration at final 1 mg/ml in Super-Block (Blocking buffer in TBS) solution; to make Biotin-Antibody at 2 µg/ml concentration (in TBS) and getting samples ready (usually 10-fold dilutions of antigen); to make 3 µg/ml concentration of Probe-Labelled antibody.
   1.3 To prepare Tris buffered saline (TBS, pH 7.6) buffer and TBS washing buffer (plus 0.05% Tween-20);
2. The procedure include:
   2.1 Add 30 µl of SA-magnetic particles, 100 µl Biotin-Antibody and 10 µl antigen from 10-fold stock dilution into each well and incubate at room temperature for 15 min under shaking (shaker 50) at 120 rpm;
   2.2 Insert the magnetic plate into 96-well microplate for four minutes to separate unbounded antigen (FIG. 8);
   2.3 Wash plate three times (3×) with TBS to wash off excess of antigen (FIG. 10);
   2.4 Remove the magnetic plate assembly (20) and add 100 µl of probe-antibody into each well, incubated for 30 minutes with gentle shaking;
   2.5 Insert the magnetic plate assembly 20 for four minutes to separate unbounded probe-antibody and wash off excess probe-antibody 3× with washing buffer;
   2.6 Remove the magnetic plate assembly (20) and add 100 µl PBS buffer in each well; shake 96-well plate at 200 rpm for 30 seconds and incubate at room temperature for 5 min before the reading. Alternatively, if alkaline phosphatase-antibody used without remove the MP, add 100 µl of fluorogenic substrate instead of 100 µl of TBS reacted for 10 minutes before the reading at specific wavelength.

By using the magnetic microplate separator of the present invention there follows several advantages, including: semi-automated, programmable process including the steps of dilution, incubation, soaking, orbital shaking, magnetic separation, bead wash, rinse and reagent dispensing. Further, this invention improves the traditional microtiter immunoassay, especially a) a system which provides a mobile solid phase that enhanced specific agent capture and separation;

b) efficiency of agent separation which is enhanced by a strong magnetic field on the side wall instead of on the bottom of the well;

c) Total microplate assay time is reduced to less than one hour compared to several hours assay time used in traditional plate absorbing based ELISA.

d) This invention minimized the sample handling requirement by hand that dramatically improved the working condition of researchers who have to handle sample was by hand.

e) After the magnetic separation from the separation device, the plate should contain antibody-antigen-antibody-dye cocktails. This plate now is ready to read fluorescence directly by a fluorescent plate reader.

f) Most important, this invention provides a new solid phase methodology that not only can be used in immunoassay but also in DNA sequencing.

While the form of apparatus herein described constitutes a preferred embodiment of this invention, it is to be understood that the invention is not limited to this precise form of apparatus and that changes may be made therein without departing from the scope of the invention, which is defined in the appended claims.

What is claimed is:

1. A magnetic microplate assembly using a microplate, the microplate including multiple wells for containing liquid under analysis formed in an array of multiple rows and columns, the wells of the microplate being integrally formed with and depending from an upper surface, the wells being generally cylindrical with spaces formed therebetween on the underneath side of the upper surface, said assembly comprising a generally flat support plate, and a plurality of magnets supported on said support plate and being spaced apart to extend upwardly into the spaces formed between the wells of the microplate when said support plate and the microplate are brought together.

2. The magnetic microplate assembly of claim 1 wherein said support plate is made of a non-magnetic material.

3. The magnetic microplate assembly of claim 1 wherein each of said magnets are cylindrical and are mounted on said plate with their axis vertical.

4. The magnetic microplate assembly of claim 3 wherein each magnet includes magnetic poles located at the ends of each of said magnets.

5. The magnetic microplate assembly of claim 4 wherein one pole of said magnets is located within the vertical extent of the microplate wells.

6. The magnetic microplate assembly of claim 1 wherein the magnets are secured to said support plate by an adhesive.

7. The magnetic microplate assembly of claim 1 wherein there are at least twenty-four magnets on said support plate for use with a ninety-six well microplate.

8. An apparatus for immunoassay using a disposable microplate, said microplate including multiple wells for containing liquid under analysis formed in an array of multiple rows and columns, the wells of the microplate being integrally formed with and depending from a relatively flat upper surface, the wells being generally cylindrical with spaces formed therebetween on the underneath side of the upper surface, said apparatus comprising means for supporting the microplate in a relatively fixed position, a reusable magnetic microplate assembly containing multiple magnets positioned for insertion in the spaces between wells underneath the microplate, and means for moving said magnetic microplate assembly relative to the microplate thereby to permit selective separation of magnetic components within the microplate wells.

9. The apparatus of claim 8 further including means for shaking said microplate supporting means.

10. The apparatus of claim 8 further including means for inserting and removing fluids from the well of the microplate.

11. A method of separating suspended magnetic particles in a microplate wherein the microplate includes multiple wells for containing liquid under analysis formed in an array of multiple rows and columns, the wells of the microplate being integrally formed with and depending from a relatively flat upper surface, the wells being generally cylindrical with spaces formed therebetween on the underneath side of the upper surface, the method comprising the steps of supporting a plurality of individual magnets on a plate with each magnet being capable of being inserted into the space between adjacent wells of the microplate, and inserting the magnet containing plate into the underneath side of the microplate.

12. The magnetic microplate assembly of claim 4 wherein the poles of said magnets alternate in polarity.

* * * * *